United States Patent [19]

Fuller et al.

[11] Patent Number: 5,610,066
[45] Date of Patent: Mar. 11, 1997

[54] NUCLEIC ACID MODIFYING PROTEINS FROM *PYROCOCCUS FURIOSUS*

[75] Inventors: Carl W. Fuller, Cleveland Heights; Joseph Szasz, Chesterland, both of Ohio; Frank T. Robb, Silver Spring; Kimberly M. Borges, Ellicott City, both of Md.; Maria Davis, Twinsburg, Ohio

[73] Assignee: Amersham Life Science, Inc., Cleveland, Ohio

[21] Appl. No.: 166,346

[22] Filed: Dec. 10, 1993

[51] Int. Cl.$^6$ .......................... C12N 15/63; C12N 15/11; C12N 15/55
[52] U.S. Cl. ................... 435/320.1; 536/23.1; 536/23.2; 536/23.7; 435/172.3; 435/69.1; 435/196; 435/252.3
[58] Field of Search .............................. 435/320.1, 252.3, 435/172.3, 69.1, 196; 536/23.1, 23.2, 23.7

[56] References Cited

U.S. PATENT DOCUMENTS 5,366,883  11/1994  Asada et al. ............................ 435/202

OTHER PUBLICATIONS

Uemori et al., "Organization and nucleotide sequence of the DNA polymerase gene from the archaeon *Pyrococcus furiosus*", 21 *Nuc. Acids Res.* 259–265, 1993.

*Primary Examiner*—Robert A. Wax
*Assistant Examiner*—Rebecca Prouty
*Attorney, Agent, or Firm*—Lyon & Lyon

[57] ABSTRACT

Purified nucleic acid comprising a nucleotide base sequence selected from sequence ID NOS.: 1-8.

2 Claims, No Drawings

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 399
        ( B ) TYPE: nucleic acid
        ( C ) STRANDEDNESS: single
        ( D ) TOPOLOGY: linear ( i i ) SEQUENCE DESCRIPTION: SEQ ID NO: 1:

```
GATAGAGAGA  AGACTGAATT  ATAAGGCGAA  GATTATTGCC  GAACACAAGG  CCGATGCAAA      60
GTATCCAGTA  GTTTCAGCAG  CTTCAATACT  TGCAAAGGTT  GTTAGGGATG  AGGAAATTGA     120
AAAATTAAAA  AAGCAATATG  GAGACTTTGG  CTCTGGGTAT  CCAAGTGATC  CAAAAACCAA     180
GAAATGGCTT  GAAGAGTACT  ACaAAAAACA  CAACTCTTTC  CCTCCAATAG  TCAGACGAAC     240
TGGGAAACTG  TAAGAAAAAT  AGAGGAAAGC  CATTAAAGCC  AAAAAATCCC  AGCTAACGCT     300
TGATAAATTC  TTTAAGAAAC  CTTAGAAAGT  CTATCCACAA  CCTTCCATAT  TCTTTGATCC     360
ACTCCCAGTA  GATCTTCAAA  GATTTTTCGA  AGTACTCCC                              399
```

( 2 ) INFORMATION FOR SEQ ID NO: 2:

(i) SEQUENCE CHARACTERISTICS:
    (A) LENGTH: 177
    (B) TYPE: nucleic acid
    (C) STRANDEDNESS: single
    (D) TOPOLOGY: linear (ii) SEQUENCE DESCRIPTION: SEQ ID NO: 2:

```
CAACTGCCTT TATTATGTCA TCTTCAAGGT TAACTGCTAT CAATCCATCG TCTGCCAATA    60
GTATTTCATT TTGAGCTTCT TCCAGCATTT CTTTGGCTTT AATGTTGAGT TCTTAATTCT   120
CTAACCACCC AAACTCTCTC AACTCCGTAC TTTGGAACGG AATTCTGCAG CCCGGGG     177
```

(2) INFORMATION FOR SEQ ID NO: 3:

(i) SEQUENCE CHARACTERISTICS:
        (A) LENGTH: 268
        (B) TYPE: nucleic acid
        (C) STRANDEDNESS: single
        (D) TOPOLOGY: linear (ix) FEATURE:
        (A) NAME/KEY: Other
        (B) LOCATION: 242...242
        (D) OTHER INFORMATION: "N"=unknown base (ii) SEQUENCE DESCRIPTION: SEQ ID NO: 3:

```
GCATTCTCTA GGGCATCGTA AACGTTCCTG CTTCCACATC TTGGACAAAC CCCTTTCTCC    60
TCCCAATCTA CGAATTGATG GCCACAGTCT CTACACCTTT TTATAGTGTC GTAGACTGGG   120
ACAAAGTATC TTTTACCCCC CCNTTTTCT AGAAGAAGAA CTCCGTGATA TCCTTCAGTA    180
GTGACTAGAT CNAACATATG TCCTCCACTT GCTAGAATCG TCAACANTTT GTCTNCAATG   240
GNAACTTCAT ATGTAACTNA ATCANCAA                                      268
```

(2) INFORMATION FOR SEQ ID NO: 4:

(i) SEQUENCE CHARACTERISTICS:
        (A) LENGTH: 288
        (B) TYPE: nucleic acid
        (C) STRANDEDNESS: single
        (D) TOPOLOGY: linear (ii) SEQUENCE DESCRIPTION: SEQ ID NO: 4:

```
GGTTAGTCTT AGAAGGCAAG ATAAGTGAAC AGGTTAAAGA CCTTGTTAAG TCTGCACTAA    60
TGATTGTGGA GAGCCCCAAC AAGGCCAGGA CAATAGCTAA CTTCTTTGGC CAGCCAAGTA   120
AAAGAAGAAT TGGTGATTTA GTTACATATG AAGTTTCCAT TGGAGACAAA ATGTTGACGA   180
TTCTAGCAAG TGGAGGACAT ATGTTTGATC TAGTCACTAC TGAAGGATAT CACGGAGTTC   240
TTCTTCTAGA AAGGGGGTAA AGATACTTTG TCCAGTCTAC GACACTAT              288
```

(2) INFORMATION FOR SEQ ID NO: 5:

(i) SEQUENCE CHARACTERISTICS:
        (A) LENGTH: 198
        (B) TYPE: nucleic acid
        (C) STRANDEDNESS: single
        (D) TOPOLOGY: linear (ii) SEQUENCE DESCRIPTION: SEQ ID NO: 5:

```
GTTTTCAAGA ACATCCATTA CTTCCTCTTC ATTTTCAATG AACGCTATCT CTGCATCTAT    60
ACTCCAAGCC TCGTTTAGAT GTCTGGTCGT ATTGTGCTCC TCAGCCCTAA AGATGGGAGC   120
TGTTTCAAAA ACTTTATCCA GCCCAGTGGC CTTCATGAGC TTACTTATAC TCCAGCCCAT   180
CATGATGAAT ATTATCAG                                                 198
```

( 2 ) INFORMATION FOR SEQ ID NO: 6:

( i ) SEQUENCE CHARACTERISTICS:
    ( A ) LENGTH: 128
    ( B ) TYPE: nucleic acid
    ( C ) STRANDEDNESS: single
    ( D ) TOPOLOGY: linear ( i i ) SEQUENCE DESCRIPTION: SEQ ID NO: 6:

```
GAATTTAACA  TACTCACTTG  GATCACTAAC  TCTACTATAG  CTTTATCAAA  TGTCTCTGGA    60
ATGTGTTTGT  AACTTAAAGG  GCCCTCGGAA  TTCCATAGTA  GTCTTCTTTT  GGCTTCATCT   120
TCTCTAGG                                                                 128
```

( 2 ) INFORMATION FOR SEQ ID NO: 7:

( i ) SEQUENCE CHARACTERISTICS:
    ( A ) LENGTH: 132
    ( B ) TYPE: nucleic acid
    ( C ) STRANDEDNESS: single
    ( D ) TOPOLOGY: linear ( i i ) SEQUENCE DESCRIPTION: SEQ ID NO: 7:

```
CCTAGAGAAG  ATGAAGCCAA  AAGAAGACTA  CTATGGAATT  GCCGAGGGCC  CTTTAAGTAC    60
AAAGACATTC  CAGAGACATT  TGATAAAGCT  ATAGTAGAGT  TAGATGATCC  AAGTGAGTAT   120
GTTGAAATTG  CG                                                           132
```

( 2 ) INFORMATION FOR SEQ ID NO: 8:

( i ) SEQUENCE CHARACTERISTICS:
    ( A ) LENGTH: 169
    ( B ) TYPE: nucleic acid
    ( C ) STRANDEDNESS: single
    ( D ) TOPOLOGY: linear ( i i ) SEQUENCE DESCRIPTION: SEQ ID NO: 8:

```
GCAAAGAAGA  AGAAAGAGGT  TGGAGTTGAA  AGATTCTACA  ATATCACCAA  CACTTATTAA    60
GAAGAACATT  CCAACTGGAA  TTGCTCCTGC  CTGCCTGCAA  AGCTCTACTA  GAGCTCTTTG   120
AGTTTCTCCA  CTTCTGACAA  CATCATCAAC  TATTAAAACT  CTCTCCCG                 169
```

NUCLEIC ACID MODIFYING PROTEINS FROM *PYROCOCCUS FURIOSUS*

This invention was made with Government support under Grant No. N00014-90-J-1823, awarded by the Department of the Navy. The Government has certain rights in this invention.

The work described in this application was to some extent supported by the U.S. government, specifically NSF Grant BCS9011583 and ONR Grant N00014-90-J-1823. The U.S. government may have rights in the invention.

BACKGROUND OF THE INVENTION

This invention relates to the cloning of nucleic acid from thermophilic organisms.

SUMMARY OF THE INVENTION

This invention features the cloning and sequencing of nucleic acid from *Pyrococcus furiosus*. Specifically, nucleic acid related to DNA modifying enzymes which have utility in several standard procedures, such as DNA sequencing, amplification (e.g., the polymerase chain reaction), mapping of target sites, and the like. See, Tabor and Richardson, U.S. Pat. Nos.: 4,795,699, 4,994,372, 4,946,786, 4,942,130, 5,145,776, 4,921,794, 5,173,411, and 5,266,466; and Mullis, U.S. Pat. Nos.: 4,683,195, 4,683,202, and 4,800,159 all hereby incorporated by reference herein. In addition, the proteins can be used in the amplification procedure of Gingeras et al., PCT/US88/02108, Kacian et al., EPA 90307503-A, EPO 408295A2 and others (also incorporated herein by reference).

In a first aspect, the invention features purified nucleic acid including a nucleotide base sequence selected from those shown as sequence ID NOS. 1–8. Preferably, such nucleic acid encodes an active nucleic acid modifying enzyme, and is cloned by standard techniques as described herein.

By "purified" is meant that the nucleic acid is isolated from the environment in which it naturally occurs, that is, from a *Pyrococcus furiosis* cell, and is preferably provided within a vector such as a plasmid, cosmid or lambda vector, in which it can be expressed in other cells, e.g., *E. coli*. Such expression will allow production of large amounts of purified nucleic acid modifying proteins which can be used in the standard methods noted above.

Other features and advantages of the invention will be apparent from the following description of the preferred embodiments thereof, and from the claims.

DESCRIPTION OF THE PREFERRED EMBODIMENTS

Over the last few years, several genera of bacteria have been discovered that grow near or above 100° C. All of these organisms are Archaea that have been isolated mainly from sulfurous geothermal marine environments. The group as a whole has many unique features such as ether-linked lipid membranes, introns and a transcriptional system more related to lower Eukaryotes (Eukarya) than to Prokaryotes. The DNA replication systems in the hyperthermophiles have not been characterized, and they are very likely to be extraordinary in comparison with other bacteria in terms of thermostability and error correction.

The hyperthermophilic microorganism, *Pyrococcus furiosus*, has the ability to survive and grow optimally at 100° C. (212° F.). Previous gene cloning and sequencing exercises demonstrated that genes could be identified by homology search with existing databases. The current invention is an example of gene discovery through sequence determination of random cDNA clones leading to the simultaneous identification and cloning of genes. The sequences of these genes, which are homologous to RNAse H, a DNA binding protein, and other nucleic acid modifying proteins, may be used in expression of these enzymes in *Escherichia coli* or other systems. They may lead to an enhanced capacity to catalyse changes to DNA and RNA that may improve gene cloning, amplification, and sequencing systems.

Example: Sequences of Random cDNA Clones

The hyperthermophilic Archeum, *Pyrococcus furiosus* DSM 3638 was grown at 98° C. in 2 L of a standard complex medium. Two 1 L cultures were harvested by centrifugation, yielding 2 g cells, wet weight. RNA was extracted by the method of DiRuggiero and Robb (DiRuggiero, J and F. T. Robb (1991) Protocols for Archaebacterial Research, eds E. Fleischmann, A. R. Place, F. T. Robb and H. J. Schreier, sect 3.4.1). The method includes a cell lysis step in 5 M guanidine thiocyanate, 10% sarkosyl (N-lauroylsarcosine, sodium salt) that inhibits RNAse activity. The RNA was phenol extracted at pH 7.0 and ethanol precipitated. After exhaustive washing with 70% ethanol, the RNA was resuspended in standard Tris/EDTA buffer at pH 7.

The RNA was random primed with hexameric oligonucleotide primers and cDNA was created using AMV reverse transcriptase (Promega). Second strand cDNA synthesis was carried out with Klenow fragment *E. coli* DNA polymerase and RNAse H1. The double stranded cDNA was ligated to EcoR1 linkers, repurified and cloned into the EcoR1 site of the Lambda ZAP vector (Stratagene, La Jolla, Calif.). A library of about $10^6$ plaque forming units was created. This library was amplified and the resulting phage lysate subjected to in vivo rescue using M13 R408 interference resistant helper phage.

The rescued library, consisting of cDNA clones in the pBluescript SK vector, was arrayed as single colonies on standard LB agar with 100 µg/ml of ampicillin. Individual clones were selected, grown overnight in 5 ml of medium and plasmid miniprep methods were used to prepare sequencing templates.

All sequencing was performed using alkaline denaturation and SEQUENASE® Version 2.0 T7 DNA Polymerase (U.S. Biochemical Corporation, Cleveland, Ohio) and 7-deaza dGTP according to standard protocols. cDNA clones in pBluescript SK vector were sequenced using standard T3 and T7 primers.

To identify the randomly sequenced cDNA sequences, homology searches were performed with the BLAST algorithm (Altschul et al., (1990), J. Mol. Biol. 215: 403–410; Gish et al., (1993) Nature Genetics 3: 266–272), using the BLAST network service of the National Center for Biotechnology Information (NCBI). Briefly, sequences were first submitted to a search by BLASTN to identify similarities in nucleotide sequence. This type of search was best at identifying ribosomal sequences. All nonribosomal sequences were submitted to a BLASTX search, which translates the sequence of interest into the six possible reading frames and compares these with a peptide sequence database. Homologies are considered to be significant if P(N) is less than 0.05—i.e., less than 5% probability of similarity occuring by random chance. For protein homologies, the codon bias of *Pyrococcus furiosus* was also taken into consideration. If a translated sequence contained multiple codons which are rare in *Pyrococcus furiosus* coding sequences, the homology was considered spurious.

The sequences were archived as, for example, 03est7, whereby clones have a two character designation, followed by est for expressed sequence tag, followed by 3 or 7 indicating the use of T3 or T7 primers, in the sequencing reactions.

Sequences identified as nucleic acid modifying proteins were the following:

| | |
|---|---|
| plest7 | reverse gyrase (SEQ. ID. NO.: 4) |
| plest3 | reverse gyrase (SEQ. ID. NO.: 3) |
| r2est7 | aspartyl-tRNA synthetase (SEQ. ID. NO.: 5) |
| w7est7 | DNA polymerase (SEQ. ID. NO.: 7) |
| w7est3 | DNA polymerase (SEQ. ID. NO.: 6) |
| w8est7 | adenine phosphoribosyl transferase (SEQ. ID. NO.: 8) |
| o3est7 | DNA binding protein (SEQ. ID. NO.: 2) |
| h3est7 | RNase H (SEQ. ID. NO.: 1) |

These partial cDNA sequences can be used as probes for isolating the complete gene sequences from a library of *Pyrococcus furiosus* genomic DNA or cDNA. It is then possible to isolate the native proteins, or cloned or recombinant proteins. For example, reverse gyrase proteins can be isolated to study DNA topology in hyperthermophiles and other organisms, or to introduce positive supercoils in DNA to study the effects on transcription, replication or stability.

The DNA polymerase partial cDNA clone w7est7 is different from that of the previously published *Pyrococcus furiosus* DNA polymerase (Uemori et al., (1993) Nuc. Acids Res. 21: 259–265). This partial sequence can be used to obtain more sequence from the genome, and the full length gene can be cloned and expressed, to determine whether this unique polymerase will be useful for cycle sequencing, or applications in which a processive thermostable polymerase is desirable.

The cDNA sequences can also be used to isolate homologous sequences from a wide variety of organisms. Although only a few such homologies at the DNA level were found in our searches, this may be due to a lack of similar sequences in the database, rather than a lack of similarity between organisms at the nucleotide level. Translation of the sequences can be used to design peptides for antibody production, or to design nucleotide probes with a codon bias similar to the organism in which the desired search is to be made.

In addition, *E. coli* RNAse H is a relatively unstable enzyme that is universally used in cDNA cloning procedures as well as transcript mapping. The thermophilic homolog would be more suitable and effective in both of these operations, due to its greater stability, leading to an immobilization formulation (readily devised by those in the art) for two new products.

DNA binding proteins may also have application in the following areas in molecular biology: altering the specificity of DNA—DNA hybridization, or DNA-RNA hybridization, which may in turn lead to improved protocols for Southern and Northern hybridization and DNA sequencing methods and DNA amplification. Improved specificity of the polymerase chain reaction may also result from the use of a thermostable DNA binding protein in the thermal cycling steps.

The modifying proteins are thus useful as substitutes in existing kits or methods using such proteins, e.g., Stratagene's "Perfect Match" product for PCR improvement.

Other embodiments are within the following claims.

We claim:

1. Purified nucleic acid comprising the nucleotide base sequence of SEQ. ID NO. 1 in a vector.

2. The purified nucleic acid of claim 1 encoding RNaseH from *Pyrococcus furiosus*.

* * * * *